United States Patent
Overstreet et al.

(10) Patent No.: US 7,805,198 B2
(45) Date of Patent: *Sep. 28, 2010

(54) OPTIMIZING PITCH AND OTHER SPEECH STIMULI ALLOCATION IN A COCHLEAR IMPLANT

(75) Inventors: Edward H Overstreet, Valencia, CA (US); Leonid M Litvak, Los Angeles, CA (US); William Vanbrooks Harrison, Tempe, AZ (US)

(73) Assignee: Advanced Bionics, LLC, Valencia, CA (US)

( * ) Notice: Subject to any disclaimer, the term of this patent is extended or adjusted under 35 U.S.C. 154(b) by 373 days.

This patent is subject to a terminal disclaimer.

(21) Appl. No.: 11/830,846

(22) Filed: Jul. 31, 2007

(65) Prior Publication Data

US 2008/0021551 A1    Jan. 24, 2008

Related U.S. Application Data

(63) Continuation of application No. 10/731,050, filed on Dec. 9, 2003, now Pat. No. 7,251,530.

(60) Provisional application No. 60/433,037, filed on Dec. 11, 2002, provisional application No. 60/523,928, filed on Nov. 21, 2003.

(51) Int. Cl.
    *A61N 1/00* (2006.01)
(52) U.S. Cl. .................................................. 607/57
(58) Field of Classification Search .............. 607/55, 607/57, 137, 56, 59; 73/585; 600/25
See application file for complete search history.

(56) References Cited

U.S. PATENT DOCUMENTS 3,751,605 A    8/1973    Michelson (Continued)

FOREIGN PATENT DOCUMENTS

WO    03/015863    2/2003

OTHER PUBLICATIONS

Harnsberger, et al., "Perceptual "vowel spaces" of Cochlear Implant Users: Implications for the Study of Auditory Adaptation to Spectral Shift", J Acoust Soc Am, vol. 109(5) pt. 1, (May 2001) pp. 2135-2145.

(Continued)

*Primary Examiner*—George Manuel
*Assistant Examiner*—Robert N Wieland
(74) *Attorney, Agent, or Firm*—Wong, Cabello, Lutsch, Rutherford & Brucculeri LLP (57) ABSTRACT

Errors in pitch (frequency) allocation within a cochlear implant are corrected in order to provide a significant and profound improvement in the quality of sound perceived by the cochlear implant user. In one embodiment, the user is stimulated with a reference signal, e.g., the tone "A" (440 Hz) and then the user is stimulated with a probe signal, separated from the reference signal by an octave, e.g., high "A" (880 Hz). The user adjusts the location where the probe signal is applied, using current steering, until the pitch of the probe signal, as perceived by the user, matches the pitch of the reference signal, as perceived by the user. In this manner, the user maps frequencies to stimulation locations in order to tune his or her implant system to his or her unique cochlea.

12 Claims, 4 Drawing Sheets

U.S. PATENT DOCUMENTS

| | | | |
|---|---|---|---|
| 4,357,497 A * | 11/1982 | Hochmair et al. | 607/5 |
| 4,400,590 A | 8/1983 | Michelson | |
| 4,495,384 A | 1/1985 | Scott et al. | |
| 4,532,930 A * | 8/1985 | Crosby et al. | 607/57 |
| 4,819,647 A | 4/1989 | Byers et al. | |
| 5,271,397 A | 12/1993 | Seligman et al. | |
| 5,526,819 A * | 6/1996 | Lonsbury-Martin et al. | 600/559 |
| 5,601,617 A * | 2/1997 | Loeb et al. | 607/56 |
| 5,603,726 A | 2/1997 | Schulman et al. | |
| 5,626,629 A * | 5/1997 | Faltys et al. | 607/57 |
| 5,749,066 A * | 5/1998 | Nussbaum | 704/232 |
| 5,794,187 A | 8/1998 | Franklin et al. | |
| 5,800,475 A * | 9/1998 | Jules | 607/57 |
| 5,860,936 A * | 1/1999 | Levin | 600/558 |
| 5,938,691 A | 8/1999 | Schulman et al. | |
| 6,002,966 A * | 12/1999 | Loeb et al. | 607/57 |
| 6,067,474 A | 5/2000 | Schulman et al. | |
| 6,068,652 A * | 5/2000 | Cohen et al. | 607/57 |
| 6,078,838 A | 6/2000 | Rubinstein | |
| 6,129,753 A | 10/2000 | Kuzma | |
| 6,157,861 A | 12/2000 | Faltys et al. | |
| 6,181,969 B1 | 1/2001 | Gord | |
| 6,195,585 B1 | 2/2001 | Karunasiri et al. | |
| 6,205,360 B1 | 3/2001 | Carter et al. | |
| 6,208,882 B1 | 3/2001 | Lenarz et al. | |
| 6,219,580 B1 | 4/2001 | Faltys et al. | |
| 6,249,704 B1 | 6/2001 | Maltan et al. | |
| 6,289,247 B1 | 9/2001 | Faltys et al. | |
| 6,295,467 B1 | 9/2001 | Kollmeier et al. | |
| 6,304,787 B1 | 10/2001 | Kuzma et al. | |
| 6,393,325 B1 * | 5/2002 | Mann et al. | 607/46 |
| 6,415,185 B1 | 7/2002 | Maltan | |
| 6,516,227 B1 | 2/2003 | Meadows et al. | |
| 6,609,032 B1 * | 8/2003 | Woods et al. | 607/46 |
| 6,731,769 B1 | 5/2004 | Lenhardt | |
| 6,915,166 B1 * | 7/2005 | Stecker et al. | 607/55 |
| 6,925,332 B2 * | 8/2005 | Franck | 607/57 |
| 6,970,570 B2 * | 11/2005 | Goldstein | 381/321 |
| 7,043,303 B1 | 5/2006 | Overstreet | |
| 7,076,308 B1 | 7/2006 | Overstreet et al. | |
| 7,082,332 B2 | 7/2006 | Blamey et al. | |
| 7,107,101 B1 | 9/2006 | Faltys | |
| 7,117,038 B1 | 10/2006 | Overstreet | |
| 7,171,272 B2 | 1/2007 | Blamey et al. | |
| 7,177,690 B2 | 2/2007 | Woods et al. | |
| 7,206,640 B1 | 4/2007 | Overstreet | |
| 7,496,406 B1 | 2/2009 | Segel et al. | |
| 2002/0128827 A1 | 9/2002 | Bu et al. | |
| 2003/0114899 A1 * | 6/2003 | Woods et al. | 607/60 |
| 2003/0171786 A1 * | 9/2003 | Blamey et al. | 607/57 |
| 2005/0209655 A1 * | 9/2005 | Bradley et al. | 607/48 |
| 2008/0221640 A1 | 9/2008 | Overstreet et al. | |

OTHER PUBLICATIONS

McDermott, et al., "Pitch Ranking with Nonsimultaneous Dual-Electrode Electrical Stimulation of the Cochlea", J Acoust Soc Am, vol. 96(1), (1994) pp. 155-162.

Rubinstein, et al., "The Neurophysiological Effects of Simulated Auditory Prosthesis Simulation", Second Quarterly Progress Report NO1-DC-6-2111.

van Wieringen, et al., "Comparison of Procedures to Determine Electrical Stimulation Thresholds in Cochlear Implant Users", Ear and Hearing, vol. 22(6), (2001) pp. 528-538.

Zeng, et al., "Loudness of Simple and Complex Stimuli in Electric Hearing", Annals of Otology, Rhinology & Laryngology, vol. 104(9), (1995) pp. 235-238.

Zhang, et al., "Loudness of Dynamic Stimuli in Acoustic and Electric Hearing", JAcoust Soc Am, vol. 102(5) Pt. 1, (Nov. 1997) pp. 2925-2934.

* cited by examiner

OPTIMIZING PITCH AND OTHER SPEECH STIMULI ALLOCATION IN A COCHLEAR IMPLANT

The present application is a Continuation of U.S. patent application Ser. No. 10/731,050, filed Dec. 9, 2003 (to be issued as U.S. Pat. No. 7,251,530 on Jul. 31, 2007), which claims the benefit of U.S. Provisional Patent Application Ser. No. 60/433,037, filed Dec. 11, 2002; and U.S. Provisional Patent Application Ser. No. 60/523,928, filed Nov. 21, 2003, which applications and patent are incorporated herein by reference in their entireties.

BACKGROUND OF THE INVENTION

The present invention relates to implantable neurostimulator systems, such as cochlear implants, and more particularly to an algorithm for use in a cochlear implant for optimizing pitch (frequency) and other speech stimuli allocation.

At present, very few cochlear implant patients are able to enjoy music. This is due, in part, to the fact that in the generation of control programs that allocate the stimuli to selected electrodes, or groups of electrodes, of the electrode array adapted to be inserted into the cochlea, no compensation is made for pitch warping.

Attempts have been made in the past to better allocate pitch based on recognizable speech stimuli, such as vowel sounds. See, Harnsberger, et al., "Perception "vowel spaces" of cochlear implant users: Implications for the study of auditory adaptation to sepctral shift," *J. Acoust. Soc. Am., Vol.* 109, No. 5, Pt. 1, pp. 2135-45 (May 2001). Such attempts to use vowel sounds have not resulted in great success.

Within the cochlea, there are two main cues that convey "pitch" (frequency) information to the patient. They are (1) the place or location of stimulation; and (2) the temporal structure of the stimulating waveform. In existing cochlear implant devices, frequency is mapped to a "place" as defined by the position of the electrode. Along the electrode array, frequencies are progressively mapped from low to high in the apical to basal direction, respectively. Unfortunately, the position of the electrode is not very precise, i.e., there are only a limited number of electrodes, e.g., 16 to 24, spread along the length of the electrode which is inserted into one of the spiraling ducts of the cochlea. Hence, mapping to a "place" within the cochlea has heretofore not been a very precise operation. Further, in existing cochlea implants, very little attention has been given to the waveform of the stimulating current, with only one or two parameters (e.g, amplitude and pulse width) being adjustable. Hence, it is seen that in existing cochlea implants, of the two main cues that convey pitch information, one ("place") has been addressed only imprecisely, and the other ("waveform") has only been addressed in a limited manner.

It is thus seen that improvements are needed in the way that a cochlear implant conveys pitch information to a user.

SUMMARY OF THE INVENTION

The present invention addresses the above and other needs by exercising more control over both the "place" where the stimulus is applied, and over the "temporal waveform structure" of the stimulus signal. The "place" of the stimulation is controlled more precisely through the use of "current steering", a technique (described in other patents and patent applications) for allowing stimulus current to effectively be applied at an almost infinite number of locations within the cochlea. The "temporal waveform structure" is controlled more precisely by allowing the cochlear implant user to make corrections and/or adjustments in the stimulus parameters so that the "pitch" perceived by the user is as true as possible, given the user's unique cochlear structure and sensitivities.

The present invention thus provides a technique for correcting errors in pitch allocation for use within a cochlear implant. Such technique advantageously provides a significant and profound improvement on the quality of sound perceived by a cochlear implant user.

In accordance with one aspect of the invention, a reference stimulus, e.g., a stimulus at a fixed frequency and amplitude, is applied to an appropriate electrode within the cochlea as a reference signal. Next, a probe signal is matched to an interval (e.g., an octave) above or below the reference signal. Matching is accomplished by allowing the user to shift the probe's frequency/spatial allocation along the array until the interval is matched to the satisfaction of the user. This shifting occurs by using current steering and/or a combination of changing the temporal modulation of the probe signal(s) with respect to the reference signal. Once matching has been accomplished, the parameters (location and waveform) of the reference and probe signals serve as an anchor point. The anchor points are then used to leap-frog across the spectrum, generating a frequency map uniquely tuned to the patient. This frequency map can then be used as a correction factor for the sound-processing paradigm used by the patient.

The present invention is particularly suited for users of cochlear implants who have been able in the past to experience hearing musical tones, and who are familiar with octaves and musical intervals. The reference signal, for example, may be the note A above middle-C (440 Hz), and the probe signals may be one octave apart, e.g., A above high-C (880 Hz) or A below middle-C (220 Hz). Persons who have familiarity with musical octaves and tones are generally able to readily recognize whether a probe signal is one octave, or multiple octaves, away from a reference signal. While octaves are, for most users, an easy interval to recognize, other musical intervals could also be used, e.g., thirds, fourths, or fifths, or other musical sequences with which the user is familiar, e.g., diatonic scales, such as major scales or minor scales.

In accordance with another aspect of the invention, a reference stimulus is likewise applied to an appropriate electrode within the cochlea as a reference signal. Simultaneously with application of the reference signal to the appropriate electrode, or in a rapid alternating fashion with application of the reference signal to the appropriate electrode, a second signal is applied to a second electrode having a location that is adjusted, e.g., using the closest physical and virtual electrodes, until the perceived sensation matches that of a certain vowel sound, or consonant sound, or other sound associated with speech stimuli with which the user is familiar. The distance between the reference electrode and the adjustable "virtual electrode" will correspond to the distance between the formants of the identified vowel, consonant, or other speech stimuli sound. This information may then be used to obtain the proper frequency-to-place alignment used in generating a frequency map uniquely tuned to the patient.

It is a feature of the invention to provide a tool for fitting a cochlear implant to a user that better allocates pitch so as to significantly improve the user's ability to perceive quality sound, e.g., music, vowel sounds, consonant sounds, or the like.

It is another feature of the invention to provide a fitting tool that allows a user to use his or her musical knowledge and abilities, or other well-recognized speech stimuli, to quickly and easily establish a frequency map that can thereafter be used by the cochlear implant to provide the user with the perception of very high quality sound.

BRIEF DESCRIPTION OF THE DRAWINGS

The above and other aspects, features and advantages of the present invention will be more apparent from the following more particular description thereof, presented in conjunction with the following drawings wherein.

Corresponding reference characters indicate corresponding components throughout the several views of the drawings.

DETAILED DESCRIPTION OF THE INVENTION

The following description is of the best mode presently contemplated for carrying out the invention. This description is not to be taken in a limiting sense, but is made merely for the purpose of describing the general principles of the invention. The scope of the invention should be determined with reference to the claims.

The present invention, as described below, relates to fitting a cochlear implant to the unique perception attributes of a particular user. A key portion of a fitting procedure relates to mapping the locations withing the cochlea where signals of different frequencies should be applied. The present invention provides a unique technique for use as part of a fitting procedure wherein a known (or readily perceivable) frequency relationship between a reference signal and a probe signal is applied to different locations within the cochlea, and the location at which the probe signal is applied within the cochlea relative to the reference signal is adjusted, using fixed and virtual electrodes, until the known (or readily perceived) frequency relationship between the reference signal and the probe signal is perceived.

In a preferred embodiment, explained in more detail below, the known relationship between the reference signal and the probe signal(s) is that of a musical octave or octaves. However, it is to be understood that the invention is not limited to using musical octaves as the known relationship between the reference and probe signal(s). Rather, it is only exemplary. Many other known (or readily perceived) frequency relationships may similarly be used. For example, speech sounds, which for most individuals are defined by known vowel sounds and consonant sounds, or other frequency-dependent sounds, may be used in accordance with the teachings of the present invention.

Speech sounds, particularly vowel sounds, are often defined in terms of "formants", where there is a fundamental formant sound, $F_0$, and related formants, $F_1$, $F_2$, etc. Similar formant-like relationships exist that may be used to define various consonant sounds. Likewise, certain tone sequences may be readily known to particular individuals based on prior experiences.

Any of the above-described speech sounds, or tone sequences, may be used with the present invention to help define the frequency mapping process used during the fitting process of a cochlear implant. For example, where vowel sounds are used, the fundamental formant $F_0$ is used as a reference signal, and the first formant $F_1$ is used as a probe signal. The $F_0$ formant is applied to a reference electrode and the $F_1$ formant is then applied to different electrodes that are a fixed and known physical distance from the reference electrode. As soon as the perceived sound is roughly correct as perceived by the individual, e.g, 80% correct, then the location at which the $F_1$ formant signal is applied is further fine tuned by using virtual electrodes. In other words, the physical electrode spacing may be used to provide a rough tuning of the desired frequency-location allocation, and then virtual electrodes may be used to provide a fine tuning of the desired frequency-location allocation.

As mentioned, a preferred embodiment of the present invention utilizes musical octaves, or other readily-perceivable musical sequences or combinations of pitches, e.g., chords, as the reference and probe signals. This preferred embodiment is described in more detail in the paragraphs that follow.

The present invention, as has been indicated, is directed to a method for better determining the pitch allocation in a cochlear implant. The method uses a reference signal and one or more probe signals that are a fixed frequency interval from the reference signal, e.g., an octave from the reference signal. A user adjusts the location and parameters of the probe signal until a "match" is perceived, i.e., until a user is satisfied that the interval is correct, or "tuned". Advantageously, most users can easily recognize octaves, or other musical intervals, or other known speech-sound intervals, and are thus able to determine when a match between the probe and reference signals occurs. Additional reference and probe signals are matched, as required. The location and parameters of the matched reference and probe signals are then used as an anchor point to help generate a frequency map that is uniquely tuned to the patient. Using such frequency map, the patient is able to experience a profound improvement in the quality of sound that can be perceived through the cochlear implant. Most users having such a frequency map are able to perceive music, for example, with a quality not heretofore available using a cochlear implant.

As previously indicated, the present invention allows a cochlear implant user to better perceive quality sound through exercising more control over both the "place" where a stimulus is applied, and over the "temporal waveform structure" of the stimulus signal. The "place" of the stimulation is controlled through the use of "current steering", a technique that allows stimulus current to effectively be applied at an almost infinite number of locations within the cochlea. The "temporal waveform structure" is controlled more precisely by allowing the cochlear implant user to make corrections and/or adjustments in the stimulus parameters so that the "pitch" perceived by the user is as true as possible, given the user's unique cochlear structure and sensitivities.

Before describing the present invention, it will first be helpful to provide an overview of the structure of a cochlear implant system. Such overview is provided below in connection with the description of FIGS. 1, 2A and 2B. Then, an overview of current steering will be provided in connection with the description of FIGS. 3A and 3B. It should be emphasized that the present invention is not directed to current steering, per se, as that is the subject of other patents and applications. Nonetheless, current steering forms an important element of the present invention because it is through current steering, or some equivalent electrical field allocation technique, that a user is able to control the "place" where a stimulus is applied. Finally, after the overview of a cochlear implant system and current steering, the present invention will be described in connection with the description of the flow chart appearing in FIG. 4.

Figure 1:
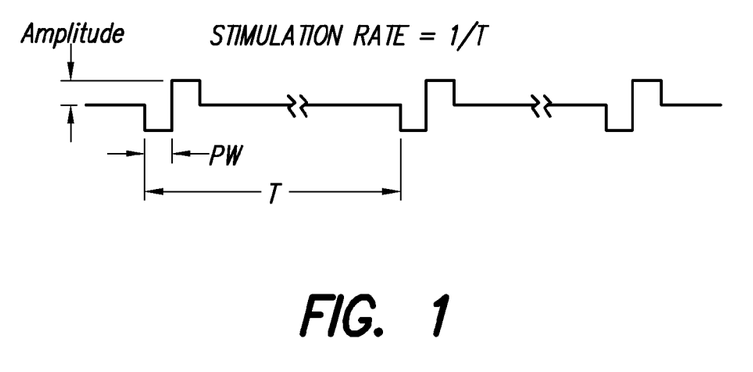
FIG. 1 is a current stimulation waveform that defines the stimulation rate (1/T) and biphasic pulse width (PW) associated with electrical stimuli, as those terms are commonly used in the neurostimulation art.

Turning, then, first to FIG. 1, there is shown a waveform diagram of a biphasic pulse train. The figure defines stimulation rate, pulse width and pulse amplitude as those terms are commonly used in connection with a neurostimulator device, such as a cochlear implant, or a spinal cord stimulator (SCS), a deep brain stimulator (DBS), or other neural stimulator. All such systems commonly generate a biphasic pulses of the type shown in FIG. 1 in order to produce a desired therapeutic effect. Although the present invention will be described in connection with a cochlear implant system, used to help the profoundly deaf to better perceive sound, it is to be understood that the invention may also be used with other types of neurostimulator systems in order to optimize the way such systems respond to input information.

Figure 2A:
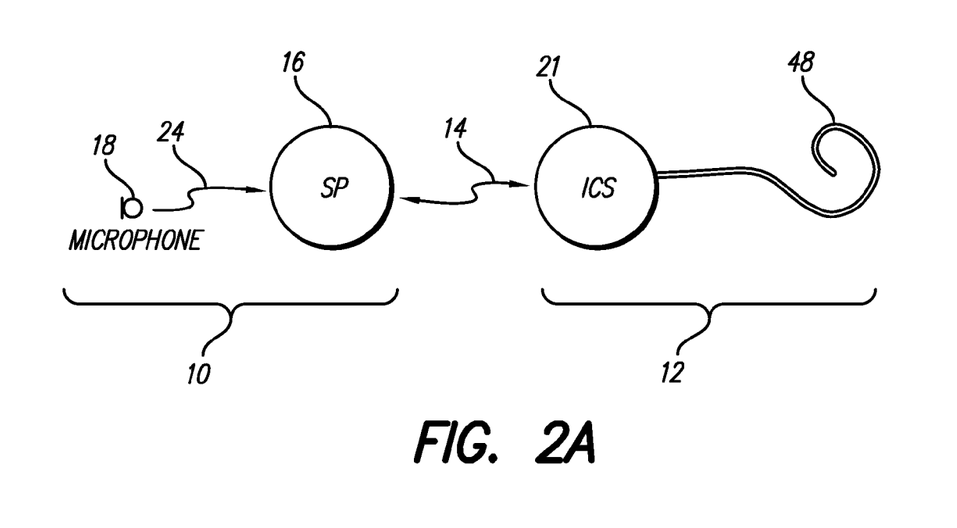
FIGS. 2A and 2B respectively show a cochlear implant system and a partial functional block diagram of the cochlear stimulation system, which system is capable of providing high rate pulsitile electrical stimuli and current steering in accordance with the invention.

FIG. 2A shows a cochlear stimulation system that includes a speech processor portion 10 and a cochlear stimulation portion 12. The speech processor portion 10 includes a speech processor (SP) 16 and a microphone 18. The microphone 18 may be connected directly to the SP 16, or may be coupled to the SP 16 through an appropriate communication link 24. The cochlear stimulation portion 12 includes an implantable cochlear stimulator (ICS) 21, and an electrode array 48. The electrode array 48 is adapted to be inserted within the cochlea of a patient. The array 48 includes a multiplicity of electrodes, e.g., sixteen electrodes, spaced along its length that are selectively connected to the ICS 21. The electrode array 48 may be substantially as shown and described in U.S. Pat. Nos. 4,819, 647 or 6,129,753, incorporated herein by reference. Electronic circuitry within the ICS 21 allows a specified stimulation current to be applied to selected pairs or groups of the individual electrodes included within the electrode array 48 in accordance with a specified stimulation pattern, defined by the SP 16.

The ICS 21 and the SP 16 are shown in FIG. 2A as being linked together electronically through a suitable data or communications link 14. In some cochlear implant systems, the SP 16 and microphone 18 comprise the external portion of the cochlear implant system; and the ICS 21 and electrode array 48 comprise the implantable portion of the system. Thus, the data link 14 is a transcutaneous data link that allows power and control signals to be sent from the SP16 to the ICS 21. In some embodiments, data and status signals may also be sent from the ICS 21 to the SP 16.

Figure 2B:
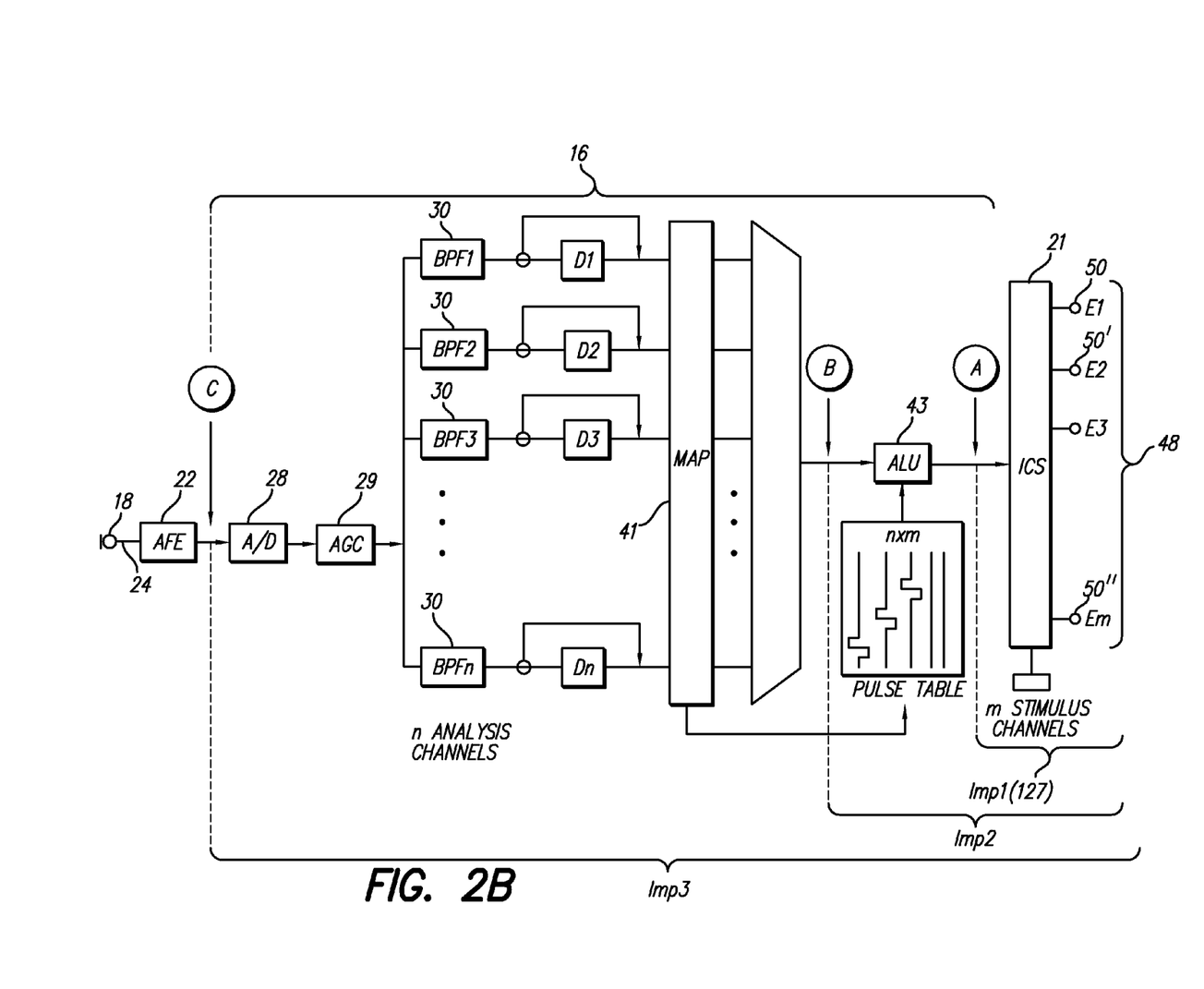

In a typical cochlear implant system, as shown more particularly in FIG. 2B, at least certain portions of the SP 16 are included within the implantable portion of the overall cochlear implant system, while other portions of the SP 16 remain in the external portion of the system. In general, at least the microphone 18 and associated analog front end (AFE) circuitry 22 will be part of the external portion of the system; and at least the ICS 21 and electrode array 48 are part of the implantable portion of the invention. As used herein, "external" means not implanted under the skin or residing within the inner ear. However, "external" may mean within the outer ear, including in the ear canal, and may also include within the middle ear.

Typically, where a transcutaneous data link must be established between the external portion and implantable portions of the system, such link is realized by an internal antenna coil within the implantable portion, and an external antenna coil within the external portion. In use, the external antenna coil is positioned so as to be aligned over the location where the internal antenna coil is implanted, allowing such coils to be inductively coupled to each other, thereby allowing data (e.g., the magnitude and polarity of a sensed acoustic signals) and power to be transmitted from the external portion to the implantable portion. Note, in other embodiments of the invention, both the SP 16 and the ICS 21 may be implanted within the patient, either in the same housing or in separate housings. If in the same housing, the link 14 may be realized with a direct wire connection within such housing. If in separate housings, as taught, e.g., in U.S. Pat. No. 6,067,474, incorporated herein by reference, the link 14 may be an inductive link using a coil or a wire loop coupled to the respective parts.

The microphone 18 senses acoustic signals and converts such sensed signals to corresponding electrical signals, and may thus be considered as an acoustic transducer. The electrical signals are sent to the SP 16 over a suitable electrical or other link 24. The SP 16 processes these converted acoustic signals in accordance with a selected speech processing strategy in order to generate appropriate control signals for controlling the ICS 21. Such control signals specify or define the polarity, magnitude, location (which electrode pair or electrode group receive the stimulation current), and timing (when the stimulation current is applied to the electrode pair) of the stimulation current that is generated by the ICS. Such control signals thus combine to produce a desired spatiotemporal pattern of electrical stimuli in accordance with the desired speech processing strategy. Unlike early cochlear implant systems, the cochlear implant system advantageously confines such control signals to circuitry within the implantable portion of the system, thereby avoiding the need to continually send or transmit such control signals across a transcutaneous link.

The speech processing strategy is used, inter alia, to condition the magnitude and polarity of the stimulation current applied to the implanted electrodes of the electrode array 48. Such speech processing strategy involves defining a pattern of stimulation waveforms that are to be applied to the electrodes as controlled electrical currents. In accordance with the present invention, current steering is employed in order to shift the location at which the current stimuli are applied to the tissue surrounding the electrode(s). If multiple electrode pairs exist, as is the case with a multichannel cochlear implant system, then the types of stimulation patterns applied to the multiple channels may be conveniently categorized as: (1) simultaneous stimulation patterns, or (2) non-simultaneous stimulation patterns. Simultaneous stimulation patterns may be "fully" simultaneous or partially simultaneous. A fully simultaneous stimulation pattern is one wherein stimulation currents, either analog or pulsitile, are applied to the electrodes of all of the available channels at the same time. A partially simultaneous stimulation pattern is one wherein stimulation currents, either analog or pulsitile, are applied to the electrodes of two or more channels, but not necessarily all of the channels, at the same time. Examples of each type are given in U.S. Pat. No. 6,289,247, incorporated herein by reference.

Analog waveforms used in analog stimulation patterns are typically reconstructed by the generation of continuous short monophasic pulses (samples). The sampling rate is selected to be fast enough to allow for proper reconstruction of the temporal details of the signal. An example of such a sampled analog stimulation pattern is a simultaneous analog sampler (SAS) strategy.

Current pulses applied in pulsitile stimulation patterns are generally biphasic pulses, as shown in FIG. 1, but may also be multiphasic pulses, applied to the electrodes of each channel. The biphasic/multiphasic pulse has a magnitude (e.g., amplitude and/or duration) that varies as a function of the sensed acoustic signal. (A "biphasic" pulse is generally considered as two pulses: a first pulse of one polarity having a specified magnitude, followed immediately, or after a very short delay, by a second pulse of the opposite polarity having the same total charge, which charge is the product of stimulus current times duration of each pulse or phase.) For multichannel cochlear stimulators of the type used with the present invention, it is common to apply a high rate biphasic stimulation pulse train to each of the pairs of electrodes of selected channels in accordance with a selected strategy, and modulate the pulse amplitude of the pulse train as a function of information contained within the sensed acoustic signal.

Turning next to FIG. 2B, a partial block diagram of a representative cochlear implant is shown. More particularly, FIG. 2B shows a partial functional block diagram of the SP 16 and the ICS 21 of an exemplary cochlear implant system capable of providing a high rate pulsitile stimulation pattern and current steering in accordance with the teachings of the present invention. That which is shown in FIG. 2B depicts the functions that are carried out by the SP 16 and the ICS 21. The actual electronic circuitry that is used to carry out these functions is not critical to understanding and practicing the present invention. It should also be pointed out that the particular functions shown in FIG. 2B are representative of just one type of signal processing strategy that may be employed (which divides the incoming signal into frequency bands, and independently processes each band). Other signal processing strategies could just as easily be used to process the incoming acoustical signal, and the present invention could still be used to provide added flexibility in specifying the stimulation patterns and waveforms that are selected and used with such additional signal processing strategies.

A complete description of the functional block diagram of the cochlear implant shown in FIG. 2B is found in U.S. Pat. No. 6,219,580, incorporated herein by reference. It is to be emphasized that the cochlear implant functionality shown in FIG. 2B is only representative of one type of exemplary cochlear implant, and is not intended to be limiting. The details associated with a given cochlear implant are not critical to understanding and practicing the present invention.

In the manner described in the U.S. Pat. No. 6,219,580 patent, the cochlear implant functionally shown in FIG. 2B provides n analysis channels that may be mapped to one or more stimulus channels. That is, as seen in FIG. 2B, after the incoming sound signal is received through the microphone 18 and the analog front end circuitry (AFE) 22, it is digitized in an analog to digital (A/D) converter 28, and then subjected to appropriate gain control (which may include compression) in an automatic gain control (AGC) unit 29. After appropriate gain control, the signal is divided into n analysis channels, each of which includes a bandpass filter, BPFn, centered at a selected frequency. The signal present in each analysis channel is processed as described more fully in the U.S. Pat. No. 6,219,580 patent, or as is appropriate using other signal processing techniques, and the signals from each analysis channel are then mapped, using mapping function 41, so that an appropriate stimulus current, of a desired amplitude and timing, may be applied through a selected stimulus channel to stimulate the auditory nerve.

Of particular relevance to the present invention, two or more stimulus channels may be selected simultaneously, with the stimulus current being dynamically weighted in an appropriate manner between the two or more channels so as to effectively steer the current from one stimulus location within the cochlea to another. The concept of current steering is taught in U.S. Pat. No. 6,393,325, incorporated herein by reference, for use within a spinal cord stimulation system. However, current steering as taught in the U.S. Pat. No. 6,393, 325 patent, may be employed within any type of neural stimulation system, including a cochlear implant system. Additional features and advantages of current steering are taught in International Publication Number WO 02/09808 A1, based on International Application Number PCT/US00/20294, filed 26 Jul. 2000, also incorporated herein by reference.

Thus it is seen that the system of FIG. 2B provides a multiplicity of channels, n, wherein the incoming signal is analyzed. The information contained in these n "analysis channels" is then appropriately processed, compressed and mapped in order to control the actual stimulus patterns that are applied to the user by the ICS 21 and its associated electrode array 48.

The electrode array 48 includes a multiplicity of electrode contacts, connected through appropriate conductors, to respective current generators, or pulse generators, within the ICS. Through these multiplicity of electrode contacts, a multiplicity of stimulus channels, e.g., m stimulus channels, exist through which individual electrical stimuli may be applied at m different stimulation sites within the patient's cochlea, or other tissue stimulation site.

While it is common to use a one-to-one mapping scheme between the analysis channels and the stimulus channels, wherein n=m, and the signal analyzed in the first analysis channel is mapped to produce a stimulation current at the first stimulation channel, and so on, it is not necessary to do so. Rather, in some instances, a different mapping scheme may prove beneficial to the patient.

For example, assume that n is not equal to m (n, for example, could be at least 20 or as high as 32, while m may be no greater than sixteen, e.g., 8 to 16). The signal resulting from analysis in the first analysis channel may be mapped, using appropriate mapping circuitry 41 or equivalent, to the first stimulation channel via a first map link, resulting in a first stimulation site (or first area of neural excitation). Similarly, the signal resulting from analysis in the second analysis channel of the SP may be mapped to the second stimulation channel via a second map link, resulting in a second stimulation site. Also, the signal resulting from analysis in the second analysis channel may be jointly mapped to the first and second stimulation channels via a joint map link. This joint link results in a stimulation site that is somewhere in between the first and second stimulation sites.

The "in between site" at which a stimulus is applied may sometimes be referred to as a virtual stimulation site. Advantageously, this possibility of using different mapping schemes between n SP analysis channels and m ICS stimulation channels to thereby produce a large number of virtual and other stimulation sites provides a great deal of flexibility with respect to positioning the neural excitation areas in a location that proves most beneficial to the patient.

More particularly, as explained in more detail below in connection with FIGS. 3A and 3B, through appropriate weighting and sharing of currents between two or more physical electrodes, it is possible to provide a large number of virtual electrodes between each physical electrode, thereby effectively steering the location at which a stimulus is applied to almost any location along the length of the electrode array.

The output stage of the ICS 21 which connects with each electrode E1, E2, E3, . . . Em of the electrode array may be as described in U.S. Pat. No. 6,181,969, incorporated herein by reference. Such output stage advantageously provides a programmable N-DAC or P-DAC (where DAC stands for digital-to-analog converter) connected to each electrode so that a programmed current may be sourced to the electrode, or sunk from the electrode. Such configuration allows any electrode to be paired with any other electrode, and the amplitudes of the currents can be programmed and controlled so as to gradually shift the stimulating current that flows from one electrode through the tissue to another adjacent electrode, or electrodes, thereby providing the effect of "shifting" the current from one or more electrodes to another electrode(s). Through such current shifting, the stimulus current may be shifted or steered so that it appears to the tissue that the current is coming from, or going to, an almost infinite number of locations.

Still with reference to FIG. 2B, it should be noted that the speech processing circuitry 16 generally includes all of the circuitry from point (C) to point (A). In prior art cochlear implant systems, the entire SP circuitry was housed in a speech processor that was part of the external (or non-implanted) portion of the system. That is, in such prior art systems, only the ICS 21, and its associated electrode array, were implanted, as indicated by the bracket labeled "Imp1" (for "Implant-1"). This means that in such prior art systems, the signal passing through the serial data stream at point (A) is also the signal that must pass through the transcutaneous communication link from the external unit to the implanted unit. Because such signal contains all of the defining control data for the selected speech processing strategy, for all m stimulation channels, it therefore has a fairly high data rate associated therewith. As a result of such high data rate, either the system operation must be slowed down, which is generally not desirable, or the bandwidth of the link must be increased, which is also not desirable because the operating power increases.

In contrast to prior art systems, a modern cochlear implant, such as the CII Cochlear implant system, or the HiRes90K implant system, manufactured by Advanced Bionics Corporation of Sylmar, Calif., advantageously puts at least a portion of the speech processor 16 within the implanted portion of the system. For example, a cochlear implant may place the Pulse Table 42 and arithmetic logic unit (ALU) 43 inside of the implanted portion, as indicated by the bracket labeled "Imp2" in FIG. 2B. Such partitioning of the speech processor 16 offers the advantage of reducing the data rate that must be passed from the external portion of the system to the implanted portion. That is, the data stream that must be passed to the implanted portion Imp2 comprises the signal stream at point (B). This signal is essentially the digitized equivalent of the modulation data associated with each of the n analysis channels, and (depending upon the number of analysis channels and the sampling rate associated with each) may be significantly lower than the data rate associated with the signal that passes through point (A). Hence, improved performance without sacrificing power consumption may be obtained with such a cochlear implant.

Future generations of cochlear implant systems will incorporate more and more of the speech processor 16 within the implanted portion of the system. For example, a fully implanted speech processor 16 would incorporate all of the SP in the implanted portion, as indicated by the bracket labeled Imp3 in FIG. 2B. Such a fully implanted speech processor offers the advantage that the data input into the system, i.e., the data stream that passes through point (C), would need only have rate commensurate with the input acoustic signal.

Additional features made possible by the cochlear implant system shown in FIG. 2B, or equivalents thereof, and which may be used in conjunction with the present invention, allow the current stimuli to be applied to the target tissue at fast rates and in a way that more naturally elicits a stochastic firing of the target tissue, as taught, e.g., in U.S. patent application Ser. No. 10/218,645 (filed Aug. 13, 2002); Ser. No. 10/218,616 (filed: Aug. 13, 2002); and 60/425,215 (filed Nov. 8, 2002); and in International Patent Application Serial No. PCT/US01/25861 (filed Aug. 17, 2002), all of which applications are assigned to the same assignee as is the present application, and all of which applications are incorporated herein by reference.

Figure 3A:
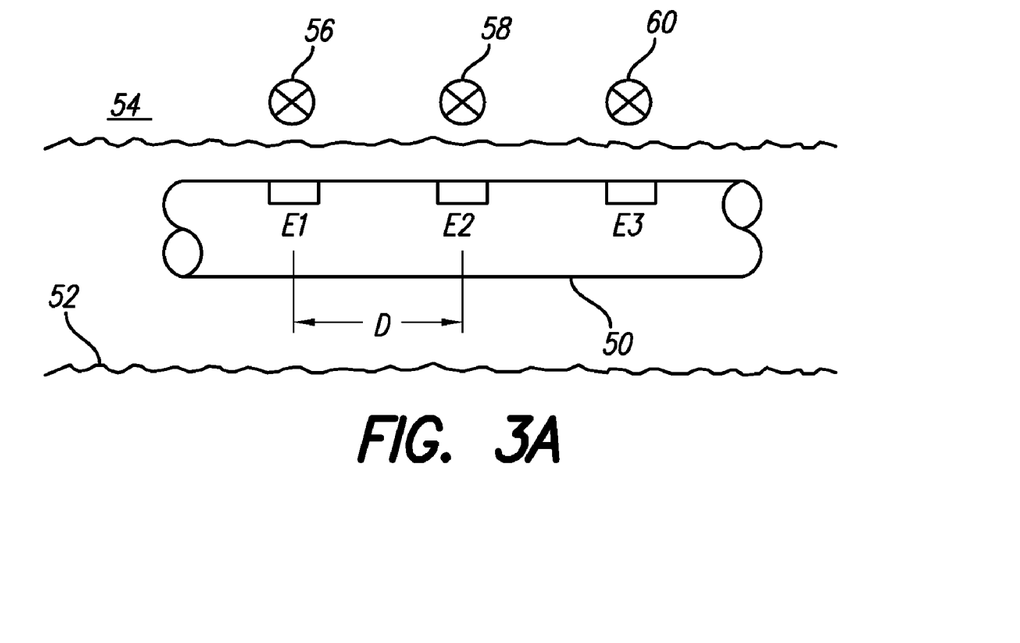
FIG. 3A schematically illustrates the location of an applied stimulus within a duct of the cochlea, or other implanted location, without the benefit of current steering.

Next, with reference to FIG. 3A, a diagram is presented to illustrate the location where a stimulus is applied when current steering is not used. In FIG. 3A, three electrodes E1, E2 and E3 of an electrode array are illustrated. A reference electrode, not shown, is also presumed to be present some distance from the electrodes E1, E2 and E3, thereby allowing monopolar stimulation to occur between a selected one of the electrodes and the reference electrode. Bipolar stimulation could likewise occur, e.g., between electrodes E1 and E2, or between E2 and E3, or between any other pair of electrodes.

The electrodes E1, E2 and E3 are located "in line" on a carrier 50, and are spaced apart from each other a known and fixed distance "D". Each electrode is electrically connected to a wire conductor (not shown) that is embedded within the carrier 50, and which connects the electrode to the ICS 21 (see FIG. 2A or 2B). The carrier 50 is shown inserted into a duct 52 within tissue 54 that is to be stimulated. For a cochlear implant system, the duct 52 typically comprises the scala tympani of a human cochlea.

When a stimulus current is applied to electrode E1, the stimulus location in the tissue 54 is essentially the location 56, adjacent the physical location of the electrode E1. Similarly, when a stimulus current is applied to electrode E2, the stimulus location in the tissue 54 is essentially the location 58, adjacent the physical location of the electrode E2. Likewise, when a stimulus current is applied to electrode E3, the stimulus location in the tissue 54 is essentially the location 60, adjacent the physical location of the electrode E3. It is thus seen that the resolution, or precision, with which a stimulus may be applied to the tissue is only as good as is the spacing of the electrodes on the electrode array. That is, each stimulus location in the tissue 54 is separated by approximately the same distance "D" as separates the electrodes.

Figure 3B:
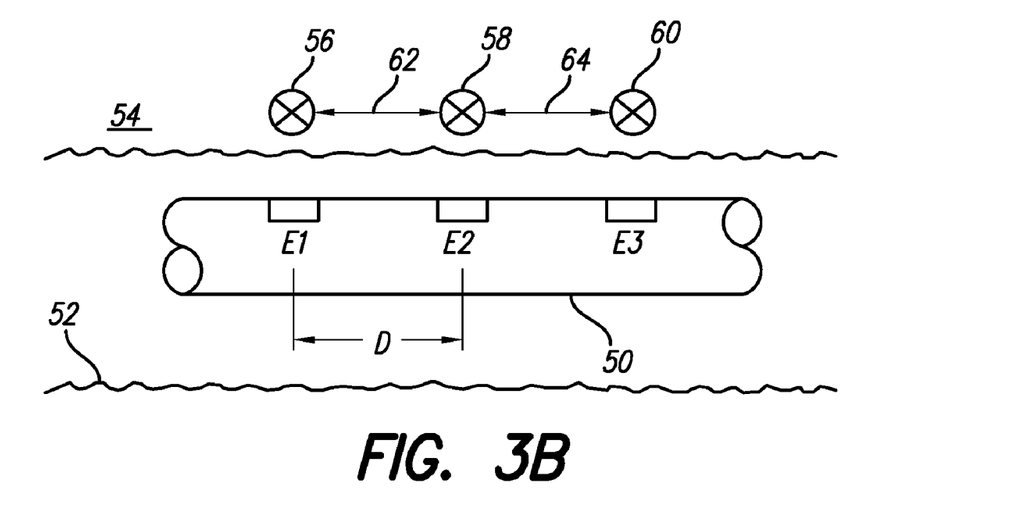
FIG. 3B schematically illustrates the location of an applied stimulus within a duct of the cochlea, or other implanted location, with the benefit of current steering.

Next, with reference to FIG. 3B, a diagram is presented to illustrate the location where a stimulus is applied when current steering is used. The structure of the electrode array and spacing between electrodes E1, E2 and E3 is the same as in FIG. 3A. Thus, when a stimulus current is applied only to electrode E1, the stimulus location in the tissue 54 is the location 56, the same as was the case in FIG. 3A. Similarly, when a stimulus current is applied only to electrode E2, the stimulus location in the tissue 54 is the location 58. Likewise, when a stimulus current is applied only to electrode E3, a stimulus location in the tissue 54 is the location 60. However, through application of current steering, a stimulus current may be shared, e.g., between electrodes E1 and E2 (and some other paired or reference electrode), and the effective tissue location where the stimulus is felt in the tissue may be anywhere along the line 62 between points 56 and 58. Alternatively, if the current is shared between electrodes E2 and E3, the location in the tissue where the stimulus is felt may be anywhere along the line 64 between points 58 and 60. The precise location where the stimulus is felt is a function of how the stimulus current is shared.

To illustrate, suppose a stimulus current having an amplitude I1 is applied to the tissue through electrode E1 (and some reference electrode). The location within the tissue 54 where the stimulus would be felt would be the point 56. However, if a stimulus current of only 0.9×I1 were applied through electrode E1 at the same time that a stimulus current of 0.1×I1 where applied through electrode E2, then the location within the tissue 54 where the stimulus would be felt would be a little to the right of the point 56, more or less somewhere on the line 62. If the stimulus current applied through electrode E1 continued to be deceased while at the same time the current applied through electrode E2 were increased, then the location in the tissue where the stimulus would be felt would move along the line 62 from left to right, i.e., from point 56 to point 58.

Similarly, by applying a current that is shared between electrodes E2 and E3, the location in the tissue where the stimulus would be felt would lie somewhere along the line 64, depending on how the current was split between the two electrodes. This concept of current sharing and current steering is described more fully in U.S. Pat. No. 6,393,325, incorporated herein by reference.

As explained previously, the location in the tissue where the stimulus is felt when current is shared between two or more electrodes may be referred to as being adjacent to a virtual electrode, where the virtual electrode may appear anywhere between the physical electrodes that share the current. Thus, it is seen that by dynamically adjusting the level, or amplitude, of the current that is shared between selected electrodes, the current can effectively be steered to any desired location between the physical electrodes. Through current steering, it is thus possible to shift the stimulation location until a desired criteria is met, e.g., until a "match" is obtained between a perceived reference signal and a perceived probe signal.

Figure 4:
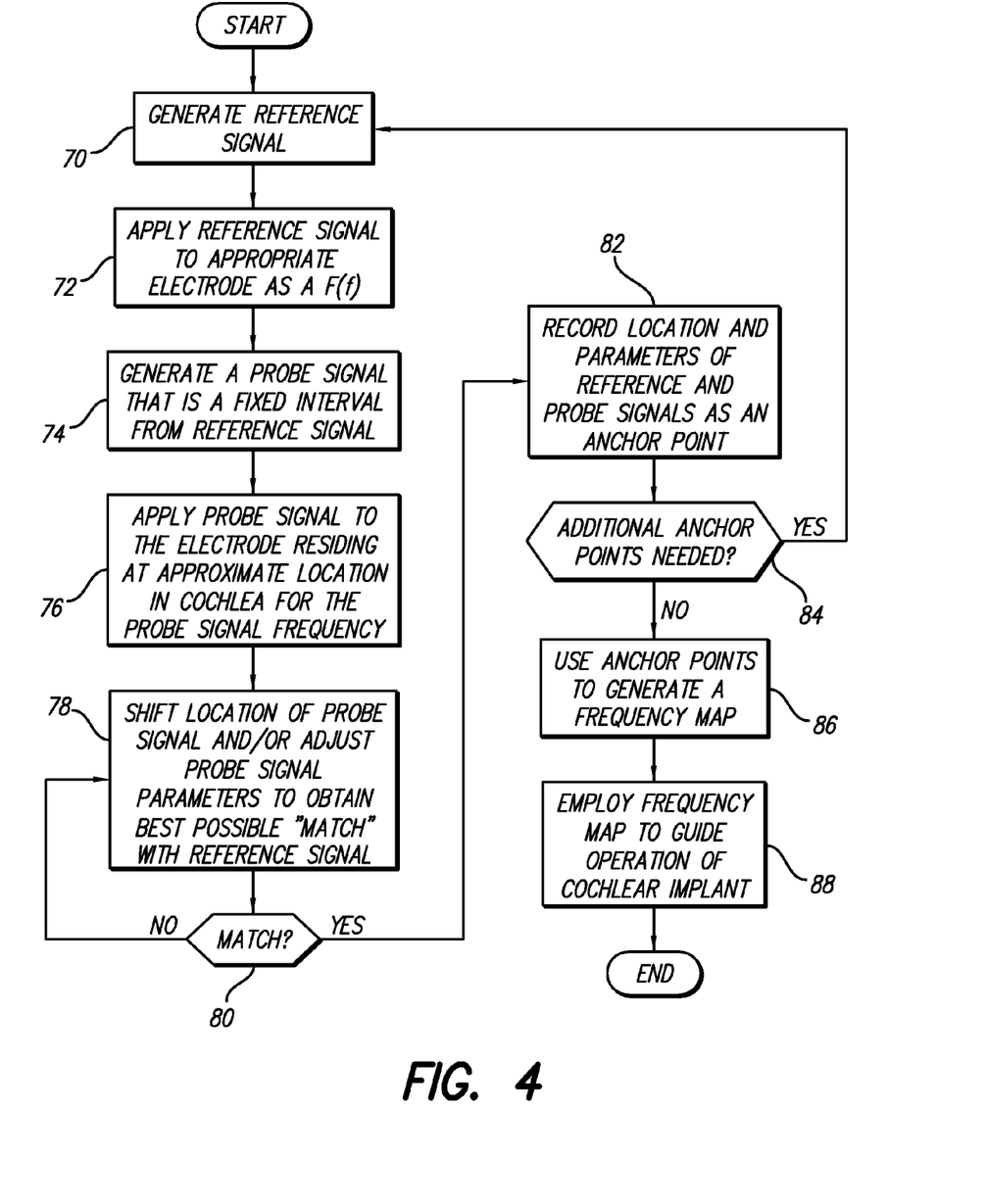
FIG. 4 is a flow chart that depicts the main steps involved in carrying out the pitch allocation technique of the present invention.

Next, the method of the present invention will be described in connection with the generalized flow chart shown in FIG. 4. Each step in the method shown in FIG. 4 is summarized in a "block". The relationship between the steps, i.e.,the order in which the steps are carried out, is represented by the manner in which the blocks are connected in the flow chart. Each block has a reference number assigned to it.

As seen in FIG. 4, a first step involves generating a reference signal (block 70). The reference signal is then applied through an appropriate electrode of the cochlear implant system so that it can be perceived by the user (block 72). Because the hair cells and ganglion cells associated with the cochlea are arranged by frequency sensitivity, e.g., with high frequencies being sensed near the basal region of the cochlea, and with low frequencies being sensed near the apical region of the cochlea, it is possible to determine approximately where in the cochlea a fixed frequency reference signal should be applied. For example, the fixed frequency reference signal may be the note "A" above middle-C (440 Hz). (The note "A" is the tone commonly used by orchestras and bands to tune their instruments.)

After the reference signal has been generated and applied to an appropriate electrode, so that it is perceived or heard by the user, a probe signal that has a fixed interval relationship with the reference signal is generated (block 74). For example, if the reference signal is the note "A", the probe signal may be one octave above the reference signal, i.e., "A" above high-C (880 Hz), or one octave below the reference signal, i.e., "A" below middle-C (220 Hz). Most individuals can readily recognize when one tone is separated from another by an octave. Hence, the octave interval is the preferred interval to use. However, as has been indicated, other readily recognized intervals may also be used, e.g., fourths or fifths, or diatonic scales, or vowel formants, or various consonant sounds, or other readily recognizable sequences or relationships.

Once the probe signal is generated, it is applied to an electrode in the cochlea residing at the approximate location in the cochlea where a signal of that frequency would be sensed (block 76). The user is thus allowed to compare the pitch of the probe signal, as perceived by the user, to the pitch of the reference signal, as perceived by the user. To facilitate such comparison, the probe signal and reference signal may be applied alternately, so that, e.g., the user listens to the reference signal for 1 second and the probe signal for 1 second. Alternatively, the user may listen to both the reference signal and probe signal simultaneously.

Next, the user shifts the location where the probe signal is applied, and/or the location where the reference signal is applied, to obtain the best possible "match" between the perceived probe signal and the perceived reference signal (block 78). Such shifting may be accomplished through current steering, or an equivalent electric field shifting technique. Additionally, the parameters associated with the reference signal, e.g., amplitude and pulse width, may be adjusted in order to improve the "match" between the two signals.

The adjustment and shifting of the probe signal and/or reference signal occurs until the best possible match is obtained (block 80). Once the best possible match has been obtained, i.e., a match with which the user is satisfied, the location and parameters of the reference and probe signals are recorded as an "anchor" point (block 82). Then, a determination is made as to whether additional anchor points are needed (block 84). If so, then another reference signal is generated (block 70) and the matching process (blocks 70-82) is repeated using the new reference signal. The new reference signal could be another note, e.g., middle-C (264 Hz), and the probe signal(s) could be high-C (528 Hz) or low-C (132 Hz).

If no more anchor points are needed (NO branch of block 84), then the data associated with each anchor point, e.g., the location and frequency, are used to generate a frequency map (block 86). The frequency map allocates a given frequency to a given stimulation location. Because the stimulation location may be a precise location, made possible through the use of current steering, such information advantageously allows the frequency map to be tuned to the user's unique anatomy. Moreover, because the probe signals have a fixed relationship with respect to the reference signal, any pitch warping that might otherwise occur within the user's inner ear, is corrected.

Once the frequency map has been generated, such map may thereafter be used to guide the operation of the cochlear implant (block 88). Advantageously, such map guides the application of the stimulus signals during normal operation of the cochlear implant so that the user enjoys hearing a quality of sound previously unavailable, including the ability to hear and enjoy music.

From the above, it is thus seen that the present invention provides a tool for fitting a cochlear implant to a user that better allocates pitch so as to significantly improve the user's ability to perceive quality sound, e.g., music.

It is also seen that the invention allows a user to use his or her musical knowledge and abilities to quickly and easily establish a frequency map that can thereafter be used by the cochlear implant to provide the user with the perception of very high quality sound.

While the invention herein disclosed has been described by means of specific embodiments and applications thereof, numerous modifications and variations could be made thereto by those skilled in the art without departing from the scope of the invention set forth in the claims.

What is claimed is:

1. A method for determining a cochlear implant frequency map that correlates audio frequencies to cochlear locations, the method comprising:

applying a first signal of a first frequency and a second signal of a second frequency to locations within a user's cochlea through a multi-electrode array implanted into the user's cochlea, wherein particular frequencies are associated with particular electrodes and wherein the first signal has a known harmonic relationship with the second signal;

shifting the location where the first signal is applied to cause the user to perceive tonal variations of the first signal;

allowing the user to select one of the tonal variations that the user perceives as best conforming to the known harmonic relationship; and determining the frequency map at least in part by using the selected tonal variation to modify the frequencies associated with the electrodes.

2. The method of claim 1, wherein the known harmonic relationship comprises the first signal being one octave above or below the second signal.

3. The method of claim 1, wherein the known harmonic relationship comprises the relationship between two notes of a musical scale.

4. The method of claim 3, wherein the musical scale comprises a diatonic scale, a major scale, or a minor scale.

5. The method of claim 1, wherein the known harmonic relationship comprises a known musical interval that separates the first frequency from the second frequency and wherein the known musical interval comprises an interval selected from the group consisting of a third, a fourth and a fifth.

6. The method of claim 1, wherein the shifting of the location where the first signal is applied comprises using current steering to change the effective location of the first signal while maintaining the location of the second signal constant.

7. The method of claim 1, wherein the first signal is a probe signal and the second signal is a reference signal.

8. The method of claim 1, wherein the first and second signals are applied simultaneously or applied alternately.

9. A method for determining a cochlear implant frequency map that correlates audio frequencies to cochlear locations, the method comprising:

applying concurrently a first signal comprising a first spectral component of a known speech sound and a second signal comprising a second spectral component of the known speech sound to locations within a user's cochlea through a multi-electrode array implanted into the user's cochlea, wherein particular frequencies are associated with particular electrodes;

shifting the location where the first signal is applied to cause the user to perceive tonal variations of the first signal;

allowing the user to select one of the tonal variations that the user perceives as best producing the known speech sound; and determining the frequency map at least in part by using the selected tonal variation to modify the frequencies associated with the electrodes.

10. The method of claim 9, wherein the known speech sound comprises a vowel sound or a consonant sound.

11. The method of claim 9, wherein the first and second spectral components are different formants of the known speech sound.

12. The method of claim 9, wherein the shifting of the location where the first signal is applied comprises using current steering to change the effective location of the first signal while maintaining the location of the second signal constant.

* * * * *